US008900060B2

(12) United States Patent
Liebing

(10) Patent No.: US 8,900,060 B2
(45) Date of Patent: Dec. 2, 2014

(54) SHAFT ARRANGEMENT HAVING A SHAFT WHICH EXTENDS WITHIN A FLUID-FILLED CASING

(75) Inventor: Reiner Liebing, Potsdam (DE)

(73) Assignee: ECP Entwicklungsgesellschaft mbH, Berlin (DE)

( * ) Notice: Subject to any disclaimer, the term of this patent is extended or adjusted under 35 U.S.C. 154(b) by 0 days.

(21) Appl. No.: 13/266,212

(22) PCT Filed: Apr. 29, 2010

(86) PCT No.: PCT/EP2010/002829
§ 371 (c)(1),
(2), (4) Date: Nov. 29, 2011

(87) PCT Pub. No.: WO2010/124882
PCT Pub. Date: Nov. 4, 2010

(65) Prior Publication Data
US 2012/0101455 A1    Apr. 26, 2012

(30) Foreign Application Priority Data

Apr. 29, 2009 (EP) .................................... 09075211

(51) Int. Cl.
*A61M 1/12* (2006.01)
*F16C 1/06* (2006.01)
*F16C 1/24* (2006.01)
*A61M 1/10* (2006.01)
*A61B 17/00* (2006.01)

(52) U.S. Cl.
CPC .. *F16C 1/06* (2013.01); *A61M 1/12* (2013.01); *A61M 1/125* (2013.01); *A61M 1/101* (2013.01); *A61B 2017/00685* (2013.01); *F16C 1/24* (2013.01)
USPC .................................. 464/7; 464/52; 604/264

(58) Field of Classification Search
USPC .......... 464/7, 17, 52, 53; 604/264, 27, 28, 35, 604/123, 151
See application file for complete search history.

(56) References Cited

U.S. PATENT DOCUMENTS 1,545,628 A * 7/1925 Wolk ............................ 464/7 X
2,679,061 A * 5/1954 Baker ......................... 464/53 X
(Continued)

FOREIGN PATENT DOCUMENTS

CA          1008330 A1   4/1977
CA          2311977 A1  12/2000
(Continued)

OTHER PUBLICATIONS

International Preliminary Report on Patentability mailed Nov. 10, 2011 for Application No. PCT/EP2010/002829 (5 pages).

(Continued)

*Primary Examiner* — Gregory Binda
*Assistant Examiner* — Matthieu Setliff
(74) *Attorney, Agent, or Firm* — Marshall & Melhorn, LLC

(57) ABSTRACT

In the case of a shaft arrangement having a shaft (7) which extends within a casing (1) filled with a fluid and which can be actuated by means of a drive (8) from outwith the casing (1), the shaft (7) having on its outer peripheral surface a surface structure which conveys the fluid in a flow direction (30) in the longitudinal direction of the shaft during rotation, a sleeve (19) is provided according to the invention, which can rotate with the shaft and has at least one conveying element (20) for conveying the fluid in a counterflow direction opposite to the flow direction. As a result, a bubble-free conveyance of the fluid along the shaft (7) is facilitated.

16 Claims, 2 Drawing Sheets

(56) References Cited

U.S. PATENT DOCUMENTS

| | | | |
|---|---|---|---|
| 3,510,229 A | 5/1970 | Smith et al. |
| 3,568,659 A | 3/1971 | Karnegis |
| 3,802,551 A | 4/1974 | Somers |
| 3,812,812 A | 5/1974 | Hurwitz |
| 4,014,317 A | 3/1977 | Bruno |
| 4,020,683 A * | 5/1977 | Young |
| 4,207,028 A | 6/1980 | Ridder |
| 4,280,338 A | 7/1981 | Shannon et al. |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A * | 8/1987 | Nash ............ 464/52 X |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,964,864 A * | 10/1990 | Summers et al. |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Scmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nusser |
| 6,860,713 B2 | 3/2005 | Hoover |
| 6,942,611 B2 * | 9/2005 | Siess |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,927,068 B2 | 4/2011 | McBride et al. |
| 7,934,909 B2 | 5/2011 | Nuesser et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0161095 A1 * | 7/2006 | Aboul-Hosn et al. |
| 2006/0195004 A1 | 8/2006 | Jarvik |
| 2008/0132747 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 | 4/2009 |
| DE | 2113986 A1 | 9/1972 |
| DE | 79 26 329 | 1/1980 |
| DE | 10155011 A1 | 5/2003 |
| DE | 102010011998 A1 | 9/2010 |
| EP | 0 347 098 | 12/1989 |
| EP | 0480102 A1 | 4/1992 |
| EP | 0560000 A2 | 9/1993 |
| EP | 0884064 A2 | 12/1998 |
| EP | 0916359 A1 | 5/1999 |
| EP | 0914171 B1 | 10/2001 |
| EP | 0768091 B1 | 7/2003 |
| EP | 0951302 B1 | 9/2004 |
| EP | 1114648 B1 | 9/2005 |

(56) References Cited

FOREIGN PATENT DOCUMENTS

| | | |
|---|---|---|
| EP | 1019117 B1 | 11/2006 |
| EP | 2 047 872 | 4/2009 |
| EP | 2343091 A1 | 7/2011 |
| FR | 1 186 539 | 8/1959 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 A1 | 10/2000 |
| WO | 0107760 A1 | 2/2001 |
| WO | 0107787 A1 | 2/2001 |
| WO | WO 01/17581 | 3/2001 |
| WO | 0183016 A2 | 11/2001 |
| WO | 03057013 A2 | 7/2003 |
| WO | 03103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

OTHER PUBLICATIONS

International Search Report and Written Opinion, from PCT/EP10/002829, mailed Oct. 13, 2010.

* cited by examiner

SHAFT ARRANGEMENT HAVING A SHAFT WHICH EXTENDS WITHIN A FLUID-FILLED CASING

FIELD OF INVENTION

The invention resides in the field of mechanics or mechanical engineering and can be used with particular advantage in precision mechanics, i.e. in the construction of small machines and appliances.

BACKGROUND OF THE INVENTION

Use in medical technology offers particular advantages, where frequently, in particular in the case of minimally invasive medical procedures, movements via shafts, in particular flexible shafts, must be transmitted through small openings or vessels occurring naturally in the body under particularly difficult surrounding conditions.

A particular type of application is represented by the actuation of liquid pumps in microconstruction, which are applied for example as heart pumps and which can be brought with a heart catheter to the operating place thereof, for example a ventricle.

For this purpose, not only do the corresponding pumps require to have a very small constructional size but also difficult conditions are present for the transmission of the pump power via a shaft. The shaft normally extends through a heart catheter and is actuated from outside the body through a leadthrough. At the distal end of the catheter, the movement is transmitted to the pump. Such shafts are usually flexible so that intensive deformations take place in particular in the case of the high speeds of rotation which are required. Therefore, not only are particularly high requirements placed upon achieving high speeds of rotation but also upon dissipating the corresponding heat which is produced by the deformation of the shaft.

A corresponding heart catheter is normally filled with a liquid which is tolerated by the body in order to lubricate the shaft, on the one hand, and to cool it, on the other hand.

Since corresponding shafts are normally composed and twisted from thinner strands in order to promote their flexibility, a spindle-shaped surface structure is produced, which, during rapid rotation, leads to conveyance of the fluid situated in the catheter along the shaft. This effect is generally undesired since it produces a pressure drop in the fluid in the catheter. From the drive-side end of the catheter, new fluid must flow along. If this is not available, then, either through the shaft leadthrough or also through a ventilation opening which can be provided likewise in the region of the catheter close to the drive and which serves for ventilating the catheter, undesired liquids or gases, for example air, can be suctioned in.

Normally, a supply line for the fluid situated in the catheter is provided, through which the fluid is pumped along by means of a pump device. It is thereby advantageous to pump a quantity of fluid which is not too large, i.e. to produce a very small volume flow. If however the pump of the fluid supply line does not provide an adequate volume flow, then a low pressure which is undesired is produced in the region of the fluid inflow as a result of the suction tendency of the shaft.

SUMMARY OF THE INVENTION

It is therefore the object of the present invention, in the case of a shaft arrangement of the initially mentioned type, to enable a prescribed bubble-free filling of the shaft arrangement with the provided fluid.

A so-called counterflow sleeve which surrounds the shaft, is disposed for example in the drive-side end region of the shaft and rotates with the latter is provided, which counterflow sleeve has at least one conveying element for conveying the fluid in a counterflow direction opposite to the flow direction.

For example, the sleeve can be connected securely to the shaft and can rotate correspondingly at the same speed of rotation as the latter. The sleeve can have, on the outside thereof, a helical blade structure or individual blades or webs in a corresponding inclined or helical construction. It is thereby important that the sleeve produces a flow or a pressure rise counter to the flow direction, i.e. in the direction of the shaft end or towards the connection chamber. As a result, a low pressure in the connection chamber and the inflow of air through a ventilation opening or the shaft leadthrough is effectively prevented. Also excessive resuctioning of the fluid is avoided, if this is delivered subsequently through a fluid inflow. By means of the sleeve, the pressure is increased towards the drive-side shaft end, whilst it is somewhat reduced on the side of the sleeve remote from the drive due to the suctioning. In this region, the conveying directions of the shaft, on the one hand, and of the sleeve, on the other hand, act against each other so that the pressure tends to drop there. In this region, there is however no inflow and no opening so that the production of gas bubbles there can be avoided.

Hence the invention has the effect that the shaft can be operated reliably at high speeds of rotation without cooling and/or lubrication by the fluid being interrupted and without gas bubbles being conveyed along the shaft towards the end of the catheter remote from the drive.

Also in the case of other uses in the non-medical field, such a bubble formation in a fluid surrounding the shaft is undesired and can be prevented with the means of the invention.

An advantageous embodiment of the invention provides that the sleeve, viewed in the flow direction, is disposed behind a connection chamber into which a leadthrough of the shaft or of a shaft drive opens.

There can be disposed in the connection chamber which is normally disposed in the drive-side end region of the shaft, additionally or alternatively to a shaft leadthrough, also a fluid supply line for the fluid filling the casing and/or a ventilation opening for ventilation of the contained fluid.

In this case, it is advantageous that a pressure drop in the connection chamber is prevented during operation by means of the sleeve in order to prevent penetration of gas bubbles or other undesired fluids or excessive resuctioning of the fluid with which the casing is filled. As a result of the arrangement of the sleeve behind the connection chamber, viewed in the flow direction, the pump effects of the sleeve and of the shaft act against each other there, i.e. in a region which is normally slightly at a spacing from the drive-side end and the connection chamber of the shaft, so that the pressure of the fluid is reduced in this region outwith the connection chamber where normally no openings are provided in the casing and hence no undesired materials can be suctioned in.

In order to ensure appropriate guidance of the sleeve during the rotational movement and to prevent, according to the type of coupling between the sleeve and the shaft, also undesired interactions between these, mounting of the sleeve on the outer circumference thereof, in particular by means of a roller bearing, can be provided advantageously. However, also a magnetic bearing or a well lubricated sliding bearing can optionally be provided there.

According to the type of bearing, also a further bearing for supporting the sleeve can be provided advantageously.

The shaft advantageously has a spindle-shaped outer contour on its surface in the longitudinal direction thereof in order to achieve the pump effect. During a rotation, in particular in the case of speeds of rotation between 20,000 and 40,000 revolutions per minute, this effects conveyance of the fluid in the longitudinal direction in addition to for instance also occurring radial and azimuthal movement directions of the fluid. This pump effect of the shaft suffices to ensure continuous cooling and lubrication. The shaft can thereby comprise for example a bundle of twisted strands, e.g. wires or fibres, in particular glass fibres, and already have, as a result, the spindle-shaped outer contour. The twisting of the individual strands is normally directed such that it corresponds with the natural twisting by applying a torque at the drive-side end so that the twisting of the shaft is stabilised during operation. This twisting direction corresponds to the spindle-shaped contour which is required for the pump direction towards the end remote from the drive.

Advantageously, the casing of the shaft can have an outlet for the fluid on the end thereof remote from the drive. In this case, the fluid there can either be discharged, for example also through a leadthrough of the shaft, e.g. if the latter continues further into a subsequently disposed pump housing, or the fluid can be pumped away at the outlet and recirculated.

In each case, the fluid, in the case of use in the medical field, will be a fluid tolerated by the body, such as for example a common salt solution, so that any quantities of liquid possibly entering into body tissue or into a blood vessel have no damaging effect.

At the corresponding outlet, the fluid can be actively suctioned out in order to prevent unintentional discharge through openings, such as for example a shaft leadthrough.

Apart from relating to a shaft arrangement of the described type, the invention also relates to a method for operating such a shaft arrangement in which the shaft rotates at a speed of at least 300 revolutions per minute. The advantageous method can provide in addition that the shaft rotates at a speed of no more than 40,000 revolutions per minute.

In addition, it can be provided that a constant flow of the fluid filling the casing is pumped into the connection chamber for cooling and lubrication of the shaft. A constant volume flow can thereby be pumped in according to the mechanism of the feeding pump or a constant pressure of the fluid can be maintained in the connection chamber. Normally, stable operating parameters are set after a short time during operation of the shaft.

The method according to the invention can provide in addition that the fluid is suctioned out of the casing of the shaft at an outlet at the end remote from the drive.

In the following, the invention is shown in a drawing with reference to an embodiment and is subsequently described.

BRIEF DESCRIPTION OF THE FIGURES

There are thereby shown

DETAILED DESCRIPTION OF THE PREFERRED EMBODIMENTS

Figure 1:
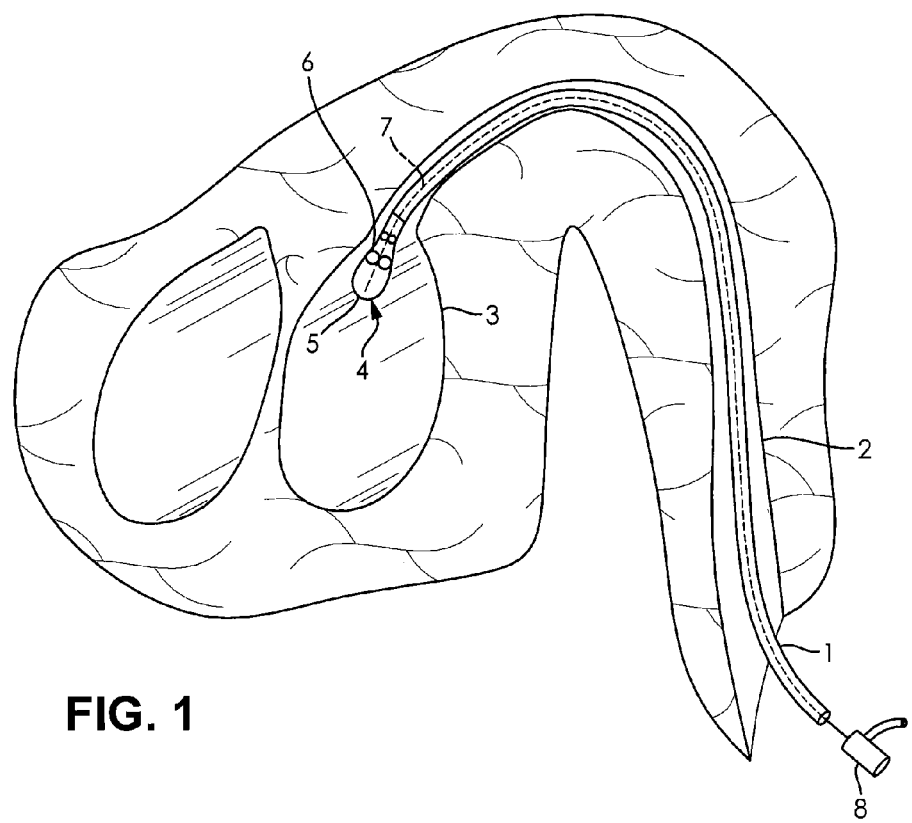
FIG. 1 a schematic overview of a catheter having a shaft which leads to a pump introduced into a ventricle, FIG. 2 schematically, a longitudinal section through the drive-side end region of a catheter with a retracted drive shaft and FIG. 3 a view of a distal end of a catheter with a shaft.

FIG. 1 shows a typical application of the shaft arrangement according to the invention in the medical field in conjunction with a heart pump. A catheter 1 is hereby provided, which is pushed through a blood vessel into a ventricle 3 and which has a micropump 4 at the distal end thereof. Said micropump has a housing 5 in which a rotor 6 can be actuated to rotate mechanically by means of a shaft 7.

The shaft 7 is guided through a leadthrough of the pump housing 5 into the catheter 1 in a sealed manner and is guided through the catheter 1 up to a shaft drive situated outwith the body in the form of a motor 8.

The pump housing 5 and the rotor 6 are normally configured in the case of such a heart catheter pump such that they can be compressed for introduction into the ventricle through the blood vessel and can be expanded within the ventricle. In order to remove the pump from the body, the latter is compressed again in order to be able to withdraw it through the vessel by means of the catheter.

The illustrated catheter is very flexible in order to be able, without injuring the blood vessel, to be guided through the bends thereof, in particular the aortic arch. Correspondingly, the shaft 7 which extends within the catheter acting as casing 1 must also be flexible. This is normally achieved in that the shaft either comprises a very flexible material and is constructed in one piece, for example as a glass or plastic material fibre, or in that it is constructed from various strands of a fairly small thickness by stranding or twisting.

In the case of a one-piece production, a corresponding surface structure can be provided during production, which surface structure effects conveyance of a fluid in the longitudinal direction at least at high speeds of rotation of the shaft. When produced by twisting, such a structure results anyway and can be used for the fluid conveyance.

In each case, at high speeds of rotation of the shaft, i.e. in particular between 20,000 and 40,000 revolutions per minute, a high deformation speed of the shaft is produced and possibly also friction between the individual elements which leads to heating of the shaft. For this reason, embedding the shaft in a liquid is sensible, which dissipates the heat, on the one hand, and, on the other hand, ensures a lubricating film between different elements of the shaft 7 or also between the shaft and the guide surrounding the latter, for example a flexible wire helix.

Such a guide can be for example a helix 9, the inner diameter of which is greater than that of the shaft and which is fixed in the catheter or placed loosely around the shaft. It is just as flexible as the catheter and produces a definite contact- and friction area for the shaft.

Figure 2:
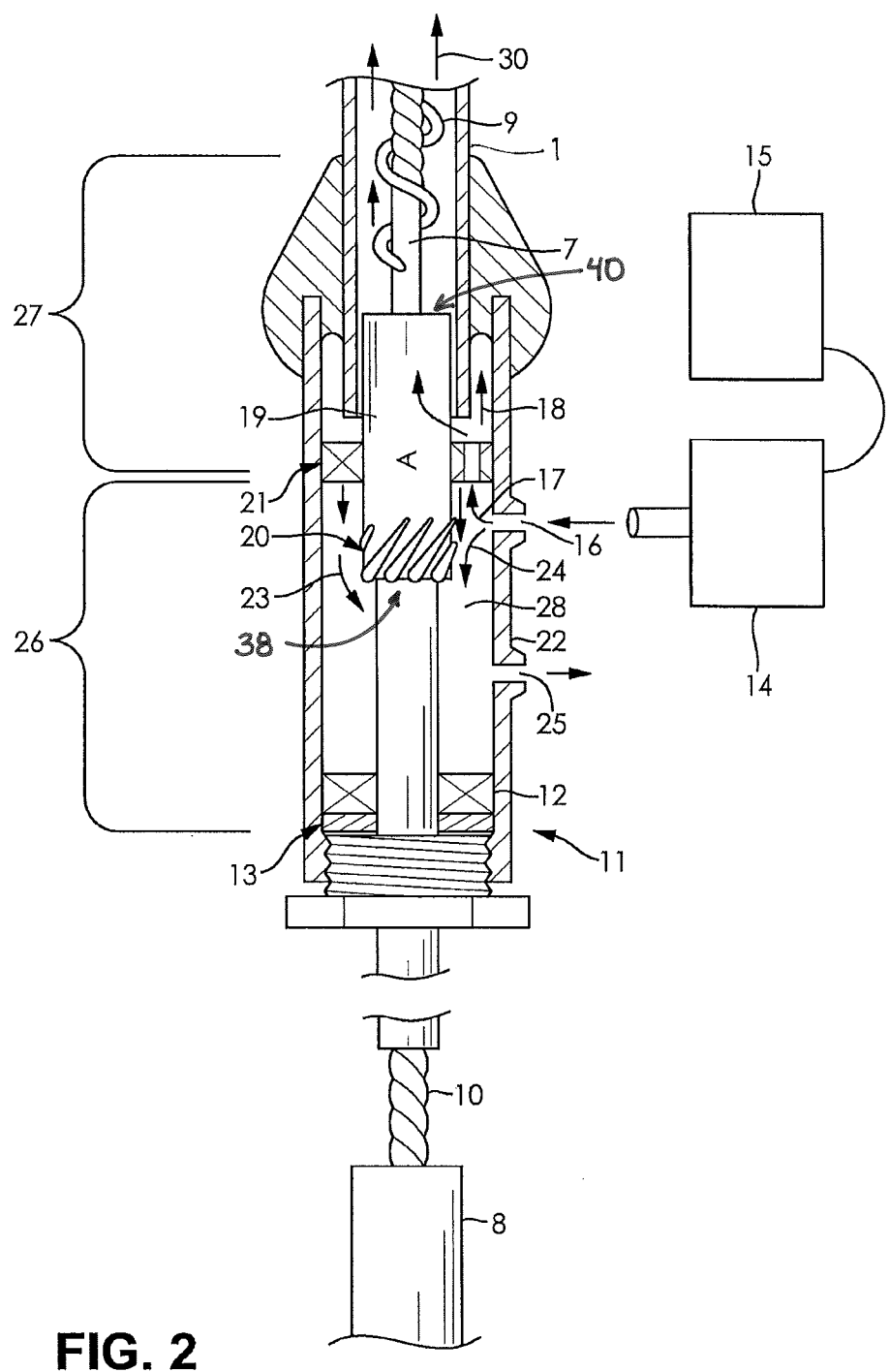

FIG. 2 shows, on a greatly enlarged scale, the drive-side end of the shaft 7 which extends in the helix 9 within the casing/catheter 1.

A motor 8 is illustrated which has a motor shaft 10 which can actually be identical to the shaft 7 or be coupled to the latter. For this purpose, one of the shafts 7, 10 can be guided through a leadthrough 11 with a bearing 12 and a packed gland 13 into the connection chamber 28. Such a leadthrough can be extensively sealed but cannot be designed to be completely sealed.

Furthermore, FIG. 2 shows a conveying pump 14 which conveys the fluid out of a reservoir 15, which fluid surrounds the shaft 7 within the catheter 1 and conveys the latter through an inflow 16 into the connection chamber 28. From here, the fluid, as represented by means of the arrows 17, 18, is conveyed along the shaft 7 in the flow direction 30 towards the distal end of the catheter 1 as long as the shaft 7 is in rapid rotation and conveys the fluid corresponding to the helical outer contour.

In addition, a sleeve 19 is represented, which sleeve has conveying elements 20 at the circumference thereof which, in the illustrated case, are defined as conveying blades which are disposed helically.

The sleeve 19 is mounted rotatably in a bearing 21 radially externally opposite the connection chamber housing 22. It is connected to the interior to shaft 7, for example via struts or via a moulding.

As seen in FIG. 2, the shaft 7 enters the sleeve 19 at a sleeve first end portion 38. The conveying element 20 is located on the sleeve first end portion 38. The shaft 7 extends through the sleeve 19 and exits the sleeve 19 at a sleeve second end portion 40. The second end portion 40 is opposite the first end portion 38. The shaft surface structure 9 is spaced from the sleeve first end portion 38.

A flow of the fluid in the direction of the arrows 23, 24 is achieved by rotation of the sleeve 19 and the function of the conveying elements 20, and in fact into the connection chamber 28. As a result, the pressure of the fluid is slightly increased in the connection chamber 28. It is consequently ensured that suctioning in of foreign liquids or gas or air is prevented both through the leadthrough 11 and through a ventilation opening 25 or the inflow 16.

As a result of the combined effect of the sleeve 19 and the conveying shaft 11, the fluid pressure is increased slightly in the region denoted with the parenthesis 26, whilst it is lowered slightly in the region of the parenthesis 27 by suction on both sides. However, no undesired fluid or gas can be suctioned in there so that altogether the formation of bubbles or penetration of foreign fluids into the catheter 1 is prevented by the features of the invention. The pump power of the sleeve 19 can be controlled by the design of the conveying elements 20 such that a balanced pump power of the shaft remains during operation and ensures a moderate flow of the fluid along the shaft 7 for cooling and lubrication purposes.

Figure 3:
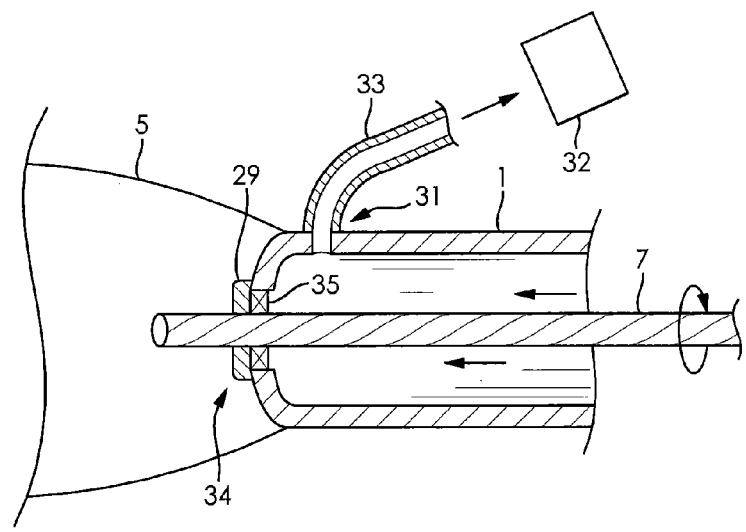

FIG. 3 shows the end of the shaft 7, which is distal or orientated away from the drive, with a leadthrough 34 out of the catheter into the pump housing 5. The leadthrough 34 provides a packed gland 29 and a bearing 35 which can be configured as a sliding bearing.

In order to ensure a fluid flow and to prevent or reduce the escape of fluid through the leadthrough 34, the fluid is suctioned through an outflow opening 31 by means of a suction pump 32 via an outflow line 33. It can be supplied again then to the reservoir 15 or be removed entirely.

Although the invention has been described in a special application in the medical field, it can be used universally, in particular in the most varied of applications of flexible shafts, e.g. in tools or machining down of components, where cooling and lubrication of the shaft by a fluid can be important.

The invention claimed is:

1. Shaft arrangement having a shaft which extends within a casing filled with a fluid and which can be actuated by means of a drive, in particular from outwith the casing, the shaft having on its outer peripheral surface a surface structure which conveys the fluid in a flow direction in the longitudinal direction of the shaft during rotation, characterised by a sleeve which is disposed in the region of the shaft, which sleeve has at least one conveying element for conveying the fluid in a direction away from the flow direction, said sleeve at least partially located within said casing, said shaft extending through a helical shaft guide fixed in said casing to an expandable pump.

2. Shaft arrangement according to claim 1, characterised in that the sleeve, viewed in the flow direction, is disposed behind a connection chamber into which a lead through of the shaft or of a shaft drive opens.

3. Shaft arrangement according to claim 1, characterised in that the sleeve is mounted in at least one bearing which surrounds the sleeve.

4. Shaft arrangement according to claim 3, characterised in that the bearing is a rotary bearing, a sliding bearing or a hydrodynamic bearing.

5. Shaft arrangement according to claim 1, characterised in that the shaft has a spindle-shaped outer contour.

6. Shaft arrangement according to claim 1, characterised in that the shaft comprises a bundle of twisted strands.

7. Shaft arrangement according to claim 1, characterised in that the casing has an outlet for the fluid at the end thereof remote from the drive.

8. Shaft arrangement according to claim 7, characterised in that the outlet is a leadthrough of the shaft.

9. Shaft arrangement according to claim 7, characterised in that the fluid at the outlet is suctioned out of the casing.

10. Method for operating a shaft arrangement according to claim 1, characterised in that the shaft rotates at a speed of at least 300 revolutions per minute.

11. Method according to claim 10, characterised in that a constant flow of fluid is pumped into a connection chamber situated at the drive-side end of the casing.

12. Method according to claim 10, characterised in that the fluid at an outlet is suctioned, at the end of the casing remote from the drive, out of the outlet.

13. Method for operating a shaft arrangement according to claim 1, characterised in that the shaft rotates at a speed of at most 40,000 revolutions per minute.

14. Shaft arrangement having a blood pump shaft which extends within a catheter filled with a fluid and which can be actuated by means of a drive at one end and having an expandable rotor for pumping blood at another end, in particular from outwith the catheter, the shaft having on its outer peripheral surface a surface structure which conveys the fluid in a flow direction in the longitudinal direction of the shaft during rotation, characterised by a sleeve which is disposed in the region of the shaft, surrounds the shaft and rotates with the latter, which sleeve has at least one conveying element for conveying the fluid in a counterflow direction opposite to the flow direction, wherein the catheter has an outlet for the fluid at the end thereof remote from the drive, said sleeve at least partially located within said catheter, said shaft extends through a helical shaft guide fixed in said catheter.

15. Shaft arrangement of claim 14, wherein the sleeve, viewed in the flow direction, is disposed behind a connection chamber into which a fluid supply line and a ventilation opening opens.

16. Shaft arrangement having a blood pump shaft which extends within a catheter filled with a fluid and which can be actuated by means of a drive at one end and having an expandable rotor for pumping blood at another end, in particular from outwith the catheter, the shaft having on its outer peripheral surface a surface structure which conveys the fluid in a flow direction in the longitudinal direction of the shaft during rotation, characterised by a sleeve which is disposed in a drive-side end region of the shaft, which sleeve has at least one conveying element for conveying the fluid in a counterflow direction opposite to the flow direction, wherein the catheter has an outlet for the fluid at the end thereof remote from the drive, said shaft extends through a helical shaft guide fixed in said catheter.

* * * * *